United States Patent [19]

Valentine, Jr.

[11] Patent Number: 5,003,093

[45] Date of Patent: * Mar. 26, 1991

[54] PROCESS FOR MAKING ALKYL ARSINE COMPOUNDS

[75] Inventor: Donald Valentine, Jr., Ridgefield, Conn.

[73] Assignee: American Cyanamid

[*] Notice: The portion of the term of this patent subsequent to Aug. 15, 2006 has been disclaimed.

[21] Appl. No.: 368,499

[22] Filed: Jun. 19, 1989

Related U.S. Application Data

[63] Continuation of Ser. No. 145,935, Jan. 20, 1988, Pat. No. 4,857,655.

[51] Int. Cl.$^5$ .................................................. C07F 9/70
[52] U.S. Cl. ........................................................ 556/70
[58] Field of Search ............................................ 556/70

[56] References Cited

U.S. PATENT DOCUMENTS 4,857,655 8/1989 Valentine .............................. 556/70

*Primary Examiner*—Gary P. Straub
*Assistant Examiner*—Stuart L. Hendrickson
*Attorney, Agent, or Firm*—Steven Flynn

[57] ABSTRACT

Alkyl arsines are made by reaction of arsine and an olefin in contact with acid catalyst. Products are mono and di-substituted arsines, e.g. alkyl and dialkyl arsines. The products contain practically no metallic or oxygenating impurities.

1 Claim, No Drawings

PROCESS FOR MAKING ALKYL ARSINE COMPOUNDS

This is a division of application, Ser. No. 07/145,935, filed Jan. 20, 1988 now U.S. Pat. No. 4,857,655.

The invention relates to improvements in the manufacture of alkyl arsines, including branched alkyl arsines and substituted alkyl arsines.

In prior art, alkyl arsines were made by multistep processes involving the reaction of organometallic compounds or lithium alkyls with inorganic arsenic compounds using oxygenated solvents such as diethyl ether. A disadvantage of such prior art processes was the difficulty of separating alkyl arsine products from impurities, particularly from oxygenated solvents or from other metallic compounds. For use of alkly arsines as arsenic source instead of arsine in metal organic chemical vapor deposition (MOCVD) processes for manufacture of semiconductor devices, there is a need to provide alkyl arsines of extremely high purity. Metallic impurities or oxygenated organic impurities can be especially detrimental to operation of electronic devices made by MOCVD processes, even when such impurities are present only in very small amounts.

The invention is a method for making alkyl arsines by catalytic reaction of an arsine and an olefin having at least three carbon atoms, without the need for metal-containing reactants or catalysts or solvents which would cause metallic or oxygenated impurities in the product. Thus, alkyl arsine products of very high purity, especially with respect to absence of metal impurities, can be obtained more easily by using the process of the invention.

According to the invention, an olefin in the presence of an acid catalyst reacts with arsine to produce mono and di-substituted arsines or with a mono-hydrocarbon substituted arsine to produce a di-substituted arsine.

Without being bound by theoretical explanation, it is supposed that the acid catalyst causes the olefin reactant to form an intermediate carbonium ion at the ethylenic double bond, which in turn reacts with the arsine reactant to form the alkyl arsine or aralkyl arsine. The carbonium ion intermediate theory is consistent with the observation that arsine does not add to a terminal carbon atom when the alkyl arsine is formed by the process of the invention.

The term olefin as used herein includes hydrocarbons having a single ethylenic double bond such as normal and branched chain aliphatic olefins, cycloaliphatic olefins, aryl substituted olefins and the like. Olefins containing at least three carbon atoms are used. Olefins containing three to 12 carbon atoms are preferred.

Normal and branched chain aliphatic olefins most preferred for making mono- and di-alkyl arsines according to the invention include, for example, propene, 1-butene, 2-butene, 2-methyl-1-propene (isobutylene), 2-methyl-1-butene, 2,3-dimethyl-1-butene, 2-ethyl-1-butene, 2-methyl-1-pentene, 2,4,4-trimethyl-1-pentene, 1-decene, 1-dodecene, 2,4,4,6,6-pentamethyl-1-heptene, and the like.

Cycloaliphatic olefins useful as olefin reactants in the invention include, for example, cyclopentene, cyclohexene, cyclooctene, 2-methylcyclopentene, 2-methylcyclohexene, and the like. Aryl substituted alkyl olefins that can be used include styrene, alpha-methylstyrene, 4-methylstyrene, and the like.

The invention is useful for making compounds which are useful as organometallic sources of arsenic to be used in processes comprising metalorganic chemical vapor deposition (MOCVD) in the manufacture of semiconductor devices such as solar cells and the like. Also, the invention is useful for making higher alkyl or aralkyl arsines which are useful as intermediates for making alkyl or aralkyl arsonic acid by oxidation of the alkyl arsine intermediates. Alkylarsonic and aralkylarsonic acids are useful for example as flotation agents in processes for concentration of tin ores.

An arsine and an olefin react by acid catalyzed addition of arsine to olefin at the double bond. When the selected olefin has a terminal ethylenic double bond, as in 1-butene, for example, the arsine adds to the second carbon atom. When an internal olefin or a cyclic olefin is selected, the addition may occur at either of the ethylenic carbon atoms. In the case of addition of arsine to a non-symetrical internal olefin, such as 2-methyl-2-butene for example, isomeric alkyl arsine products are to be expected.

The acid catalyst may be an organic or inorganic non-ozidizing strong acid such as alkanesulfonic acids, e.g. methanesulfonic acid, ethanesulfonic acid, arylsulfonic acids, e.g. benzenesulfonic acid, toluenesulfonic acid, trifluoroacetic acid, phosphoric acid, sulfuric acid, hydrogen fluoride and the like. Lower alkanesulfonic acids containing 1 to 4 carbon atoms are preferred.

As non-oxidizing strong acid catalysts for the process of the invention we may use solid or liquid acid catalysts in contact with at least the olefin reactant. The acid may be dissolved in the olefin or in solution with the olefin in a single phase liquid system. For example, the olefin may be dissolved in a hydrocarbon solvent with a hydrocarbon-soluble acid such as octane sulfonic acid or dodecylbenzene sulfonic acid. The single phase liquid is contacted with gaseous arsine under pressure to carry out the reaction.

The acid may be a solid or a liquid which is immiscible with the organic liquid phase containing the olefin reactant. When an immiscible liquid catalyst is used, it may be a liquid non-oxidizing strong acid such as $H_3PO_4$ or it may be an aqueous solution of a non-oxidizing strong acid.

When a monoalkyl arsine is used as the arsine reactant, that arsine may be in solution with the olefin.

In a preferred embodiment of the invention the reaction is carried out with arsine gas in contact with a liquid which has two immiscible liquid phases. One liquid phase is an aqueous phase which contains the acid catalyst. Arsine is dissolved to some extent in this aqueous phase. The other liquid phase is an organic phase which contains the olefin, and an organic solvent when a solvent is used. To increase the reaction rate the two liquid phases can be mixed efficiently by vigorous agitation as by stirring during the reaction. Use of an organic solvent is preferred as a vehicle for the olefin reactant and as a solvent for the alkyl arsine products. A large amount of the acid catalyst in aqueous solution is used to increase the amount of catalyst in contact with the organic phase during the reaction. To avoid oxidation of arsine reactant and the alkyl or aralkyl arsine products, oxidizing agents are excluded from the reactor.

Use of an inert organic solvent for the olefin reactant and the alkyl arsine products is preferred but not always necessary. Inert hydrocarbons having boiling points above 60° C. are preferred solvents. Paraffinic hydrocarbons such as the normal and branched alkanes having 6 to 12 carbon atoms are suitable solvents. A solvent having boiling point well apart from those of the monoalkyl and dialkyl arsine products should be selected for ease of product separation.

The addition reaction is preferably carried out under pressure when either reactant is a gas. Reactor pressures in the range from about 7 to 70 atmospheres will usually be suitable in such cases. The reactor is conveniently pressurized with arsine when arsine gas is the arsine reactant. It is preferred to use a liquid inert solvent for gaseous olefins. A molar excess of arsine to olefin is maintained during the reaction. Reaction temperatures in the range from about 25° C. to 100° C. may be used and a reaction temperature from 60° to 95° C. is usually preferred.

A convenient reactor for the process of the invention is an autoclave with stirring means for constant agitation of the reaction mixture during the reaction. The time for reaction will depend upon selected reactants and reaction conditions. About four hours is sufficient under the conditions used in the examples described below.

EXAMPLE 1

An autoclave reactor having approximately 3.8 liter capacity is charged with 400 grams of isobutylene reactant, 600 grams of n-octane solvent and 1000 grams of aqueous 70% methanesulfonic acid catalyst. The reactor is pressurized to about 12.3 atmospheres at room temperature by addition of arsine reactant in molar excess with respect to isobutylene. The autoclave is sealed and its contents are heated at 80°-95° C. with constant agitation for four hours reaction time. The contents are then cooled to 8° C. before the reactor is opened. Unreacted arsine is vented from the reactor. By gas chromatographic analysis of the liquid reaction product mixture, yields of 350 grams mono-1,1-dimethylethylarsine (36.6% yield) and 85 grams bis(1,1-dimethylethyl)arsine (6.3% yield) are measured. The organic phase separated from the liquid product mixture is washed with water, dried and then distilled at 68°-69° C. to separate the mono-1,1-dimethylethylarsine. The bis(dimethylethyl)arsine is separated by further distillation of the reaction product.

EXAMPLES 2-8

By the process described in Example 1, except with variations as shown in Table 1, other monoalkyl and dialkyl arsines are synthesized.

TABLE 1

| Example | Olefin Reactant | Arsine Reactant | Solvent | Catalyst | Products |
|---------|-----------------|-----------------|---------|----------|----------|
| 1 | isobutylene | $AsH_3$ | n-octane | methanesulfonic acid | mono- and bis (1,1-dimethylethyl) arsines |
| 2 | 2-methyl-1-butene | $AsH_3$ | n-octane | methanesulfonic acid | mono- and bis (1,1-dimethylpropyl) arsines |
| 3 | 2-methyl-1-pentene | $AsH_3$ | n-decane | ethanesulfonic acid | mono- and bis-(1,1-dimethylbutyl) arsines |
| 4 | 2,4,4-trimethyl-1-pentene | $AsH_3$ | n-octane | methanesulfonic acid | mono- and bis-(1,1,3,3-tetramethylbutyl) arsines |
| 5 | 2,4,4,6,6,-pentamethyl-1-heptene | $AsH_3$ | dodecane | butanesulfonic acid | mono- and bis-(1,1,3,3,5,5-hexamethylmexyl) arsines |
| 6 | 2-methyl-1-heptene | $AsH_3$ | n-octane | methanesulfonic acid | mono- and di-(1,1-dimethylhexyl) arsines |
| 7 | 1-decene | $AsH_3$ | n-octane | ethanesulfonic acid | mono- and di-(1-methylnonyl) arsines |
| 8 | isobutylene | 1-methylethyl* arsine | n-octane | methanesulfonic acid | 1-methylethyl-1,1-dimethylethylarsine |

*The 1-methylethylarsine reactant is dissolved in the organic liquid phase and the autoclave is operated at autogenic pressure.

Examples of compounds that can be produced by the process of the invention include but are not limited to mono 1-methylethylarsine, mono 1-methylpropylarsine, mono 1,1-dimethylethylarsine, mono 1-methylbutylarsine, mono 1,1-dimethylpropylarsine, mono 1,1-dimethylbutylarsine, mono 1,1-diethylethylarsine, mono 1,1,2-trimethylpropylarsine, mono 1,1,3,3-tetramethylbutylarsine, mono 1-methylheptylarsine, mono 1-methylnonylarsine, mono α-methylbenzylarsine, mono α,α-dimethylbenzylarsine, mono α-methyl(4-methylbenzyl)arsine, bis(1-methylethyl)arsine, bis(1-methylpropyl)arsine, bis(1,1-dimethylethyl)arsine, bis(1-methylbutyl)arsine, bis(1,1-dimethylpropyl)arsine, bis(1,1-dimethylbutyl)arsine, bis(1,1,3,3,-tetramethylbutyl)arsine, bis( α-methylbenzyl) arsine and the like.

In some embodiments of the invention an olefin is reacted with a mono alkylarsine to form dialkylsubstituted arsines. For example, isobutylene is reacted, respectively, with mono 1,1-dimethylethylarsine to form bis(1,1-dimethylethyl)arsine, with mono 1-methylethylarsine to form 1-methylethyl-1,1-dimethylethylarsine, and mono methylarsine to form methyl, 1,1-dimethylethylarsine. Additional examples of dialkyl substituted arsines that may be prepared by such combination of reactants include but are not limited to methyl-1-methylpropylarsine, methyl-1,1-dimethylpropylarsine, 1-methylethyl-1,1-dimethylpropylarsine and the like.

The monoalkyl and dialkyl arsine products obtained by the process of the invention can be readily separated from the liquid reaction product mixture by phase separation and distillation of the organic phase. The very high purity requirements for use of the alkylarsines in MOCVD may require subsequent further purification, which can be readily accomplished by redistillation. Because no metal-containing reactants have been used for the synthesis, there is no need for removal of metals from products made by the process of the invention.

We claim:

1. A process for catalytic alkylation of an arsine having at most one alkyl group and at least two hydrogen atoms, said process comprising the reaction of said arsine with an aliphatic or arylaliphatic olefin having only one olefinic double bond and 3–12 carbon atoms, wherein said arsine and olefin reactants are reacted in contact with a solid non-oxidizing strong acid catalyst.

* * * * *